United States Patent
Kulaga et al.

(10) Patent No.: US 10,399,723 B2
(45) Date of Patent: Sep. 3, 2019

(54) CONTAINER TREATMENT SYSTEM

(71) Applicant: Plasmology4, Inc., Scottsdale, AZ (US)

(72) Inventors: Emilia M. Kulaga, Scottsdale, AZ (US); Steven A. Myers, Scottsdale, AZ (US); Marc C. Jacofsky, Phoenix, AZ (US); Jeffrey I. Meyers, Phoenix, AZ (US)

(73) Assignee: PLASMOLOGY4, INC., Scottsdale, AZ (US)

( * ) Notice: Subject to any disclaimer, the term of this patent is extended or adjusted under 35 U.S.C. 154(b) by 65 days.

(21) Appl. No.: 15/068,087

(22) Filed: Mar. 11, 2016

(65) Prior Publication Data

US 2016/0264274 A1     Sep. 15, 2016

Related U.S. Application Data

(60) Provisional application No. 62/131,801, filed on Mar. 11, 2015.

(51) Int. Cl.
| | |
|---|---|
| *A61L 2/14* | (2006.01) |
| *B65B 55/02* | (2006.01) |
| *B65B 55/04* | (2006.01) |
| *B65B 55/12* | (2006.01) |
| *H01J 37/32* | (2006.01) |

(Continued)

(52) U.S. Cl.
CPC ............. *B65B 55/12* (2013.01); *A61L 2/14* (2013.01); *A61L 2/24* (2013.01); *H01J 37/32394* (2013.01); *H05H 1/2406* (2013.01); *H05H 2001/2412* (2013.01);
(Continued)

(58) Field of Classification Search
CPC ........... A61L 2/14; B65B 55/02; B65B 55/04; B65B 55/12
See application file for complete search history.

(56) References Cited

U.S. PATENT DOCUMENTS

| | | |
|---|---|---|
| 6,099,523 A | 8/2000 | Kim et al. |
| 6,361,748 B1 | 3/2002 | Prinz et al. |

(Continued)

FOREIGN PATENT DOCUMENTS

| | | |
|---|---|---|
| DE | 19532105 A1 | 3/1996 |
| DE | 102008045507 A1 | 4/2009 |

(Continued)

OTHER PUBLICATIONS

Sohbatzadeh et al., Inactivation of Aspergillus flavus spores in a sealed package by cold plasma streamers, Jan. 25, 2016.

(Continued)

*Primary Examiner* — Kevin Joyner
(74) *Attorney, Agent, or Firm* — Fletcher Yoder, P.C.

(57) ABSTRACT

A system includes a cold plasma applicator configured to couple directly to a container, wherein the cold plasma applicator is configured to generate a cold plasma within the container. A method includes operating a cold plasma applicator to generate a cold plasma to treat contents within a container, wherein the cold plasma applicator is configured to directly couple to the container, or the cold plasma applicator comprises a varying geometry application surface having a plurality of protruding electrode portions spaced apart from one another to define a plurality of intermediate recessed portions, or a combination thereof.

20 Claims, 11 Drawing Sheets

(51) Int. Cl.
*A61L 2/24* (2006.01)
*H05H 1/24* (2006.01)

(52) U.S. Cl.
CPC .............. *H05H 2001/2418* (2013.01); *H05H 2001/2437* (2013.01); *H05H 2245/1225* (2013.01)

(56) References Cited

U.S. PATENT DOCUMENTS

| | | |
|---|---|---|
| 7,633,231 B2 | 12/2009 | Watson |
| 7,679,027 B2 | 3/2010 | Bogatu |
| 8,372,460 B2 | 2/2013 | Meyers et al. |
| 2008/0142057 A1 | 6/2008 | Yan et al. |
| 2008/0179286 A1* | 7/2008 | Murokh .................. A61L 2/14 216/67 |
| 2008/0260578 A1 | 10/2008 | Engemann et al. |
| 2010/0087812 A1 | 4/2010 | Davison et al. |
| 2010/0178198 A1* | 7/2010 | Moisan .................. A61L 2/14 422/23 |
| 2011/0095688 A1 | 4/2011 | Bisges et al. |
| 2011/0180732 A1 | 7/2011 | Hirasawa et al. |
| 2012/0046597 A1 | 2/2012 | Morrill et al. |
| 2012/0046602 A1 | 2/2012 | Morrill et al. |
| 2012/0271225 A1 | 10/2012 | Stieber et al. |
| 2012/0296265 A1 | 11/2012 | Dobrynin et al. |
| 2013/0022514 A1 | 1/2013 | Morrill et al. |
| 2013/0068226 A1 | 3/2013 | Watson et al. |
| 2013/0072861 A1 | 3/2013 | Watson et al. |
| 2013/0345620 A1* | 12/2013 | Zemel .................. A61B 18/042 604/24 |

FOREIGN PATENT DOCUMENTS

| | | |
|---|---|---|
| WO | 2008082297 A1 | 7/2008 |
| WO | 2011/055113 A1 | 5/2011 |
| WO | 2012106735 A2 | 8/2012 |

OTHER PUBLICATIONS

N.N. Misra et al., In-package atmospheric pressure cold plasma treatment of strawberries, Journal of Food Engineering, Oct. 28, 2013.

N. Misra et al., In-Package Atmospheric Pressure Cold Plasma Treatment of Cherry Tomatoes, School of Food Science and Environmental Health, Mar. 17, 2014.

PCT International Search Report & Written Opinion; Application No. PCT/US2016/022122; dated May 12, 2016; 12 pages.

* cited by examiner

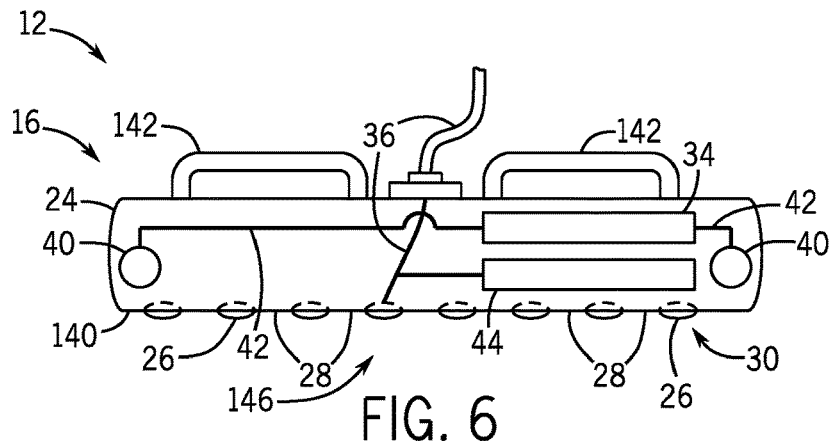
FIG. 6
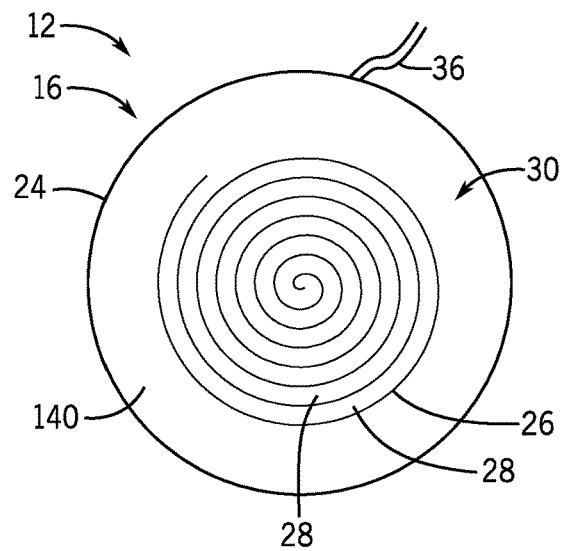
FIG. 7
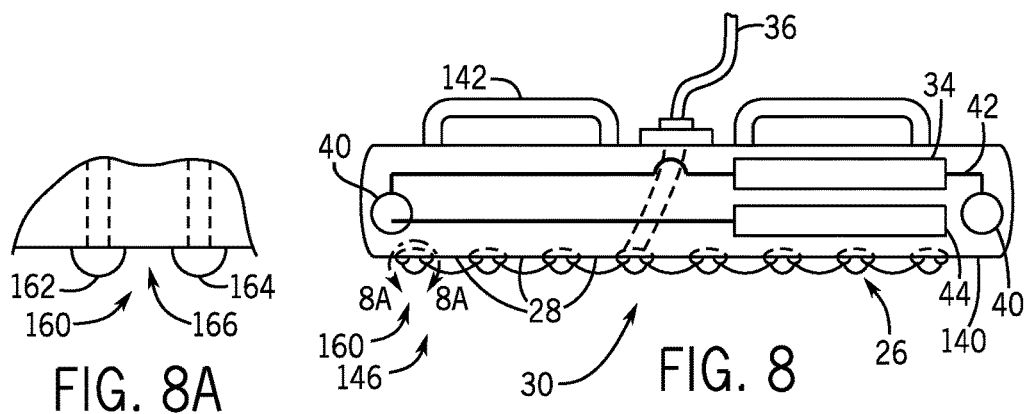
FIG. 8A
FIG. 8

CONTAINER TREATMENT SYSTEM

CROSS-REFERENCE TO RELATED APPLICATIONS

This application claims priority to and benefit of U.S. Provisional Application No. 62/131,801 entitled "Container Treatment System," filed on Mar. 11, 2015, which is hereby incorporated by reference in its entirety. This application also incorporates by reference the following applications in their entirety: U.S. Non-Provisional application Ser. No. 14/575,791 entitled "System and Method for Plasma Treatment Using Directional Dielectric Barrier Discharge Energy System", filed on Dec. 18, 2014; and U.S. Non-Provisional application Ser. No. 14/292,158 entitled "Wearable Cold Plasma System", filed on May 30, 2014.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Modern products are frequently stored and shipped in a variety of packaging or containers. The packaging or containers are typically used to protect the contents, prevent cosmetic damage, preserve freshness, and/or block contaminants. Unfortunately, once sealed the packaging or container may prevent sterilizing and/or sanitizing of the contents without reopening the package or container.

BRIEF DESCRIPTION OF THE DRAWINGS

Various features, aspects, and advantages of the present invention will become better understood when the following detailed description is read with reference to the accompanying figures in which like characters represent like parts throughout the figures, wherein:

FIG. 6 is a side view of an embodiment of a cold plasma applicator used in the systems of FIGS. 1-5, illustrating a portable unit with handles, a controller, sensors, and a spaced electrode pattern on a cold plasma application side;

FIG. 7 is a top view of an embodiment of a cold plasma applicator used in the systems of FIGS. 1-5, illustrating an embodiment of the spaced electrode pattern of FIG. 6 having an electrode coil;

FIG. 8 is a side view of an embodiment of a cold plasma applicator used in the systems of FIGS. 1-5, illustrating a portable unit with handles, a controller, sensors, and a spaced electrode pattern with a pair of adjacent electrodes (e.g., pair of adjacent electrode coils);

FIG. 8A is a partial side view of the cold plasma applicator of FIG. 8, illustrating a close-up view of one pair of adjacent electrodes (e.g., pair of adjacent electrode coils) in the spaced electrode pattern;

DETAILED DESCRIPTION OF SPECIFIC EMBODIMENTS

Figure 1:
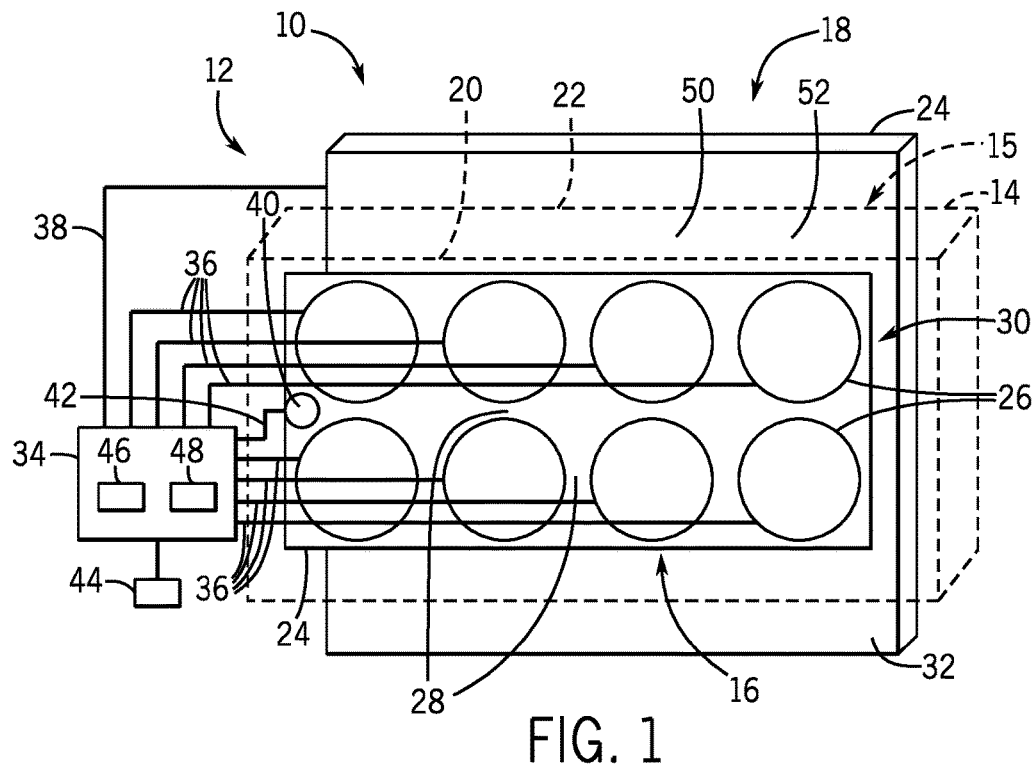
FIG. 1 is a schematic side view of an embodiment of a cold plasma treatment system configured to treat a container with cold plasma.

One or more specific embodiments of the present invention will be described below. These described embodiments are only exemplary of the present invention. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The disclosed embodiments include a cold plasma treatment system capable of sterilizing and/or sanitizing a sealed or semi-sealed dielectric (e.g., paper, plastic, or any combination thereof) package or container (e.g., disposable and/or reusable container) with a cold plasma. For example, the package or container may include flexible bags, rigid containers, cans, boxes, bottles, jars, drums, or any combination thereof. The package or container may be seamless and/or exclude any removable cover or resealable opening, or the package or container may include a removable cover or opening. By sterilizing and/or sanitizing the contents within the container, the cold plasma system may clean products (e.g., surgical instruments and other medical devices), preserve freshness of various contents (e.g., food), extend the shelf life of perishable items (e.g., food), and/or block contaminants from negatively affecting a user (e.g., kill bacteria) without opening the container or package. The food may include both animal or human food such as meat, milk and dairy products, cat food, dog food, fruits, vegetables, juices, breads, etc. The cold plasma formed by the cold plasma treatment system is a non-thermal (e.g., has a temperature between approximately 60-80, 70-90, 80-100, 90-110, 100-120 degrees Fahrenheit), multi-frequency, harmonic-rich plasma. The cold plasma is formed using a multi-frequency, harmonic-rich signal (e.g., a timed pulse electrical signal that is pulsed between 100-900 Hz with an output voltage between 1-100 kV peak-peak having multiple A/C waves at multiple frequencies that overlap to produce 2-2,000,000 or more harmonic components between DC and 500 MHz).

In operation, the multi-frequency, harmonic-rich electrical signal passes through a gas in the container (e.g., atmospheric gases, helium, neon, argon, krypton, xenon, radon, air, oxygen, nitrogen, or any combination thereof) causing gas molecules/atoms to lose and gain electrons, which produces a cold plasma with positive ions, negative ions, and electrons. It is believed that the multi-frequency, harmonic-rich electrical signal facilitates removal of electrons from molecules/atoms with less energy than typical plasma formation. Accordingly, the plasma is a low temperature plasma or cold plasma (e.g., a cold plasma with a temperature between approximately 60-120, 60-80, 70-90, 80-100, 90-110, 100-120 degrees Fahrenheit), enabling exposure to a temperature sensitive target substrate (e.g., biological tissue, food, medical instruments/tools, etc.).

FIG. 1 is a schematic side view of an embodiment of a cold plasma treatment system 10. As illustrated, the cold plasma treatment system 10 may include a cold plasma applicator 12 configured to be positioned adjacent (e.g., directly couple to and/or contact) a container or package 14. The cold plasma applicator 12 may include a first applicator portion 16 and a second applicator portion 18 disposed about opposite sides of the container 14 in a treatment space or region 15. The first and second applicator portions 16 and 18 may be stationary or portable, but are spaced apart from one another to receive the container 14. For example, the first applicator portion 16 may be disposed adjacent (e.g., in direct contact to) a first side 20 of the container 14, and on the opposite side of the container 14, the second applicator portion 18 in direct contact to a second side 22. The first applicator portion 16 may include an insulative applicator support 24 (e.g., an electrically insulative sheet, plate, etc.) configured to secure one or more electrodes 26 (e.g., powered electrode) along the first side 20 of the container 14. The one or more electrodes 26 may or may not directly contact the first side 20 of the container 14. For example, there may be a dielectric material coated on the one or more electrodes 26, such that the one or more electrodes 26 do not directly contact the container 14 as will be discussed below. For example, the one or more electrodes 26 may be embedded inside of the applicator support 24, such that a portion of the applicator support 24 is between the one or more electrodes 26 and the container 14, and the one or more electrodes 26 do not directly contact the container 14. For example, the container 14 may be made of an electrically insulative material (e.g., a dielectric material) such that the container 14 may act as a dielectric barrier and no additional dielectric coating on the one or more electrodes 26 is required.

The one or more electrodes 26 may be spaced along the applicator support 24 with an electrode gap 28 between any pair of the one or more electrodes 26 to define a spaced electrode pattern 30. In one example, the electrode gap 28 may be a constant value such that the one or more electrodes 26 are arranged in a uniformly spaced electrode pattern 30. In another example, the electrode gap 28 may vary for any pair of the one or more electrodes 26, such that the spaced electrode pattern 30 is irregular or non-uniform (e.g., not repetitive). The second applicator portion 18 may also include an insulative applicator support 24 to secure an electrode 32 (e.g., ground electrode) while the electrode 32 may or may not directly contact the second side 22 of the container 14. In addition, the one or more electrodes 26 of the first applicator 16 may couple to a controller 34 (e.g., an electronic controller or computing device) via first conductors 36 (e.g., electrical conductor, electrical cable, high power/radio frequency HV/RF cable, etc.), and the electrode 32 of the second applicator 18 may couple to the controller 34 via a second conductor 38.

Furthermore, the cold plasma treatment system 10 may include one or more sensors 40 disposed at various locations (e.g., on various components of the cold plasma treatment system 10) and coupled to the controller 34 via sensor line(s) 42. The one or more sensor 40 may monitor useful information, such as voltage, current, voltage waveforms, current waveforms, gas flow rate, gas concentration, positional data, plasma generation, plasma concentration, plasma intensity, plasma distribution, along with any other parameters disclosed herein, to monitor, characterize, analyze, and/or control the cold plasma. Based on the monitored and/or analyzed data from the one or more sensors 40, the controller 34 may adjust the operation of the cold plasma treatment system 10 accordingly. For example, the controller 34 may adjust the frequency, voltage, shape of the waveform of the pulse electrical signal coming from the power supply 44, the distance between the one or more electrodes 26 and the ground electrode 32, etc. based on the feedback form the one or more sensors 40.

In operation, the powered one or more electrodes 26 of the first applicator portion 16 receive the multi-frequency, harmonic-rich electrical signal from the controller 34 and generate cold plasma to treat contents inside the container 14. For example, the controller 34 may couple to a power supply 44 and include one or more processors 46 and one or more memories 48. The controller 34 uses the processor 46 to execute instructions stored in the memory 48 to produce and control the cold plasma generating electrical signal (e.g., change power, amplitude, frequency/frequencies, pulse timing, etc.). In some embodiments, the electrical signal may be a multi-frequency harmonic-rich signal (e.g., a timed pulse electrical signal that is pulsed between 100-900 Hz with an output voltage between 1-100 kV peak-peak having multiple A/C waves at multiple frequencies that overlap to produce 2-2,000,000 or more harmonic components between DC and 500 MHz). As the multi-frequency, harmonic-rich electrical signal passes through gases 50 within the container 14 (e.g., atmospheric gases), the gas molecules/atoms lose and gain electrons to produce cold plasma with positive ions, negative ions, and electrons. These ions and electrons in the cold plasma may then sanitize and/or sterilize the products or contents 52 within the container 14. The cold plasma may also produce radio frequency (RF) energy and reactive species (e.g., combinations of helium, oxygen, OH ions) that facilitate killing of contaminants (e.g., bacteria). As discussed above, sterilizing and/or sanitizing the contents 52 of the container may clean products (e.g., surgical instruments and other medical devices), preserve freshness of various contents 52 (e.g., food), extend the shelf life of perishable items (e.g., food), and/or block contaminants from negatively affecting a user (e.g., kill bacteria). Moreover, the cold plasma may not increase the temperature of the contents 52 in a way that alters the contents 52 (e.g., melts). As explained above, the cold plasma may have a temperature between approximately 60-120, 60-80, 70-90, 80-100, 90-110, or 100-120 degrees Fahrenheit).

In operation, the electrode 32 of the second applicator portion 18 may be a powered electrode or unpowered ground. For example, the electrode 32 of the second applicator portion 18 may couple to the controller 34, which may adjust the voltage on the electrode 32 to increase the attraction of the cold plasma and energy through the container 14. In other words, the electrode 32 may assist in guiding and/or drawing electrons in the plasma stream and energy generated by the one or more electrodes 26 of the first applicator portion 16 through the container 14 and its contents 52. In some embodiments, the cold plasma treatment system 10 may include additional powered electrodes 26 and/or additional ground electrodes 32 on additional sides of the container 14. In other embodiments, the cold plasma treatment system 10 may use some or all of the contents 52 of the container 14 as ground. For example, when sanitizing or sterilizing a metal medical device/tool, the device/tool may act as ground that attracts the multi-frequency, harmonic-rich electrical signal and therefore the cold plasma. In still other embodiments, the powered electrodes 26 and/or the ground electrode 32 may be included and/or positioned within the container 14 to focus cold plasma within the container 14.

Figure 2:
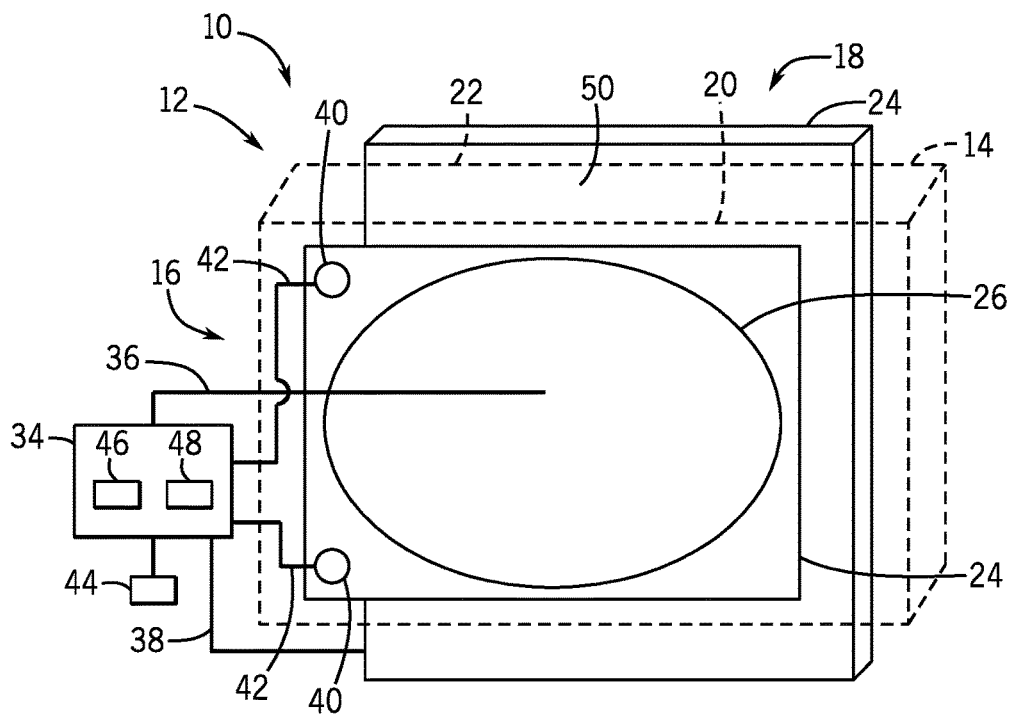
FIG. 2 is a schematic side view of an embodiment of a cold plasma treatment system configured to treat a container with cold plasma.

FIG. 2 is a schematic side view of an embodiment of a cold plasma treatment system 10, which has substantially all features of the embodiment of FIG. 1. However, in contrast to the cold plasma treatment system 10 in FIG. 1, the cold plasma treatment system 10 in FIG. 2 has the first applicator portion 16 with a single powered electrode 26 covering or substantially covering the entire first side 20 of the container 14. Accordingly, the single powered electrode 26 may then generate cold plasma throughout the container 14. In some embodiments, the cold plasma treatment system 10 may include additional powered electrodes that cover or substantially cover some or all of the other sides of the container 14.

Figure 3:
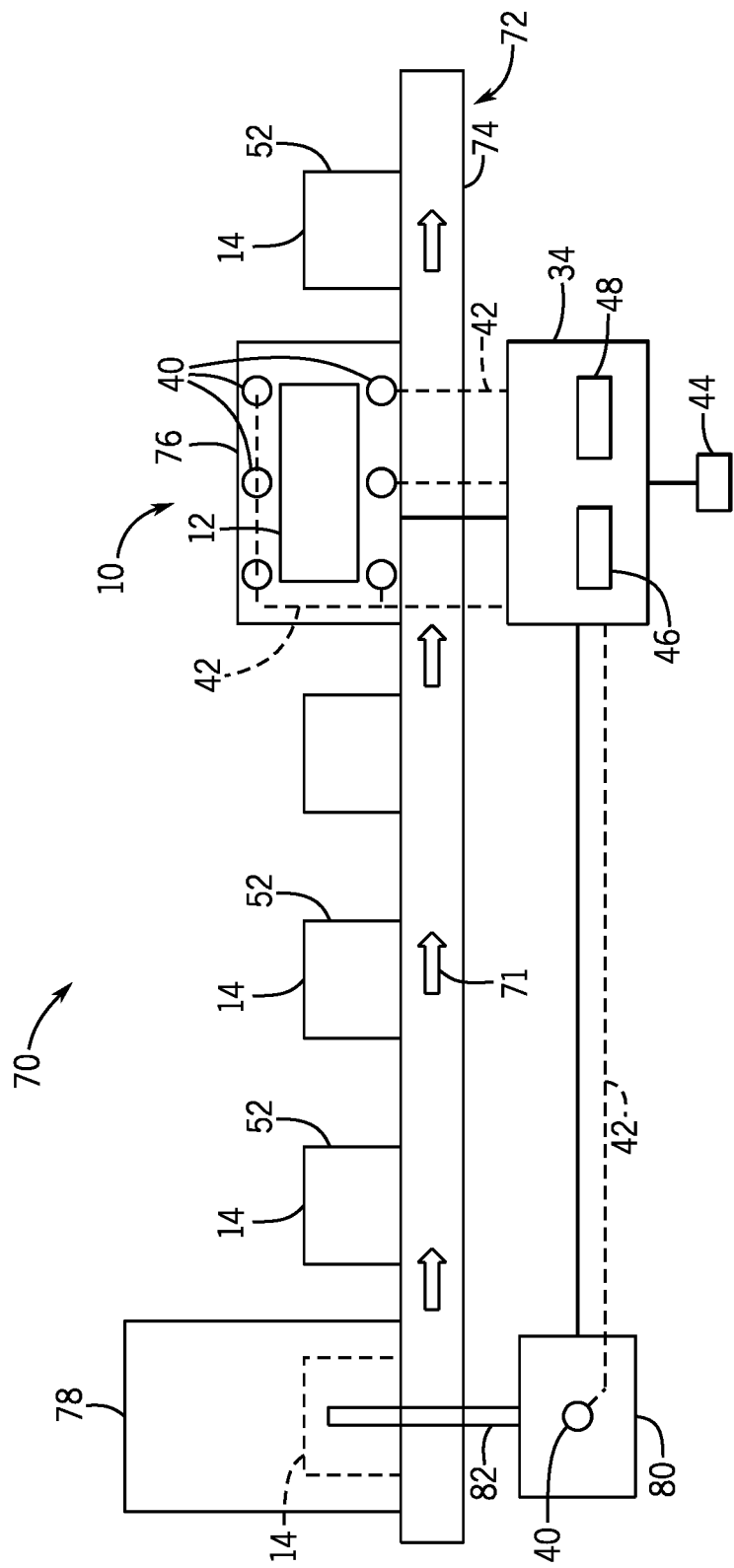
FIG. 3 is a schematic side view of an embodiment of a cold plasma treatment system disposed in an automated packaging system.

FIG. 3 is a schematic side view of an automated packaging system 70 including the cold plasma treatment system 10 described in FIGS. 1 and 2 for treating container(s) 14 on an assembly line 72. As illustrated, the containers 14 may be carried by a carrying medium such as an automated conveyor 74 (e.g., conveyor belt) and move along the assembly line 72 to be treated by the cold plasma treatment system 10. For example, the cold plasma treatment system 10 may include a cold plasma treatment housing 76 and the cold plasma applicator 12 coupled or attached to an interior or exterior of the cold plasma treatment housing 76. As previously described, the cold plasma is generated in a space between the electrodes 26 and 32 of the first and the second applicator portions 16 and 18 of the cold plasma applicator 12. As such, while the cold plasma applicator 12 is attached to the cold plasma treatment housing 76, the cold plasma may be generated throughout the containers 14 as well as the space outside of the container 14 but inside of the cold plasma treatment housing 76. For example, both an interior and an exterior of each of the containers 14 may be treated, cleaned and/or sanitized by the cold plasma treatment system 10. In other embodiments as discussed below, the cold plasma applicator 12 may be directly coupled or attached to the container 14 instead of the cold plasma treatment housing 76.

In addition, the automated packaging system 70 may include a container sealing system 78 upstream of the cold plasma treatment system 10 relative to an assembly line moving direction 71. The container sealing system 78 may include a gas source 80 controlled by the controller 34 to inject a gas or gas mixture into the container 14 via a gas supply conduit 82 before sealing to facilitate plasma generation and/or facilitate specific types of reactive species generation within the container 14. The gas or gas mixture may include an inert gas, helium, neon, argon, krypton, xenon, radon, oxygen, nitrogen, air, or any combination thereof. As previously described, the one or more sensors 40 may be disposed at various locations throughout the cold plasma treatment system 10 (e.g., on the cold plasma applicator 12 and/or on the cold plasma treatment housing 76), and in certain embodiment, the one or more sensors 40 may also be coupled to the gas source 80 or the gas supply conduct 82 to monitor useful information/parameters, such as voltage, current, voltage waveforms, current waveforms, gas flow rate, gas concentration, positional data, along with any other parameters disclosed herein to characterize or analyze the plasma generated. Based on the monitored and/or analyzed data from the one or more sensors 40, the controller 34 may also adjust the operation of the cold plasma treatment system 10 accordingly as described above.

It may also be appreciated that any of the components and/or subsystems included in the automated packaging system 70 (e.g., the container sealing system 78, the cold plasma treatment system 10, the automated conveyor 74, and components included thereof such as the cold plasma applicator 12, the one or more sensors 40, the gas source 80, etc.) may be coupled to and controlled by the controller 34 individually and/or collectively. For example, the controller 34 may send electric signal(s) to control the conveying/rolling speed and pulsation of the automated conveyor 74, and coordinate the operations performed by the container sealing system 78 and the cold plasma treatment system 10 such that the packaging and treatment/cleaning/sanitizing of the containers 14 may be coordinated collectively. It may also be appreciated that the controller 34 may adjust the operating parameters of the cold plasma treatment system 10 as described above and collectively adjust the operating parameters of the container sealing system 78. For example, the controller 34 may analyze the characteristics of the plasma generated based on feedback from the one or more sensors 40 and determine to change to composition and/or increase or decrease the amount of the gas being supplied from the gas source 80 to the container 14.

Figure 4:
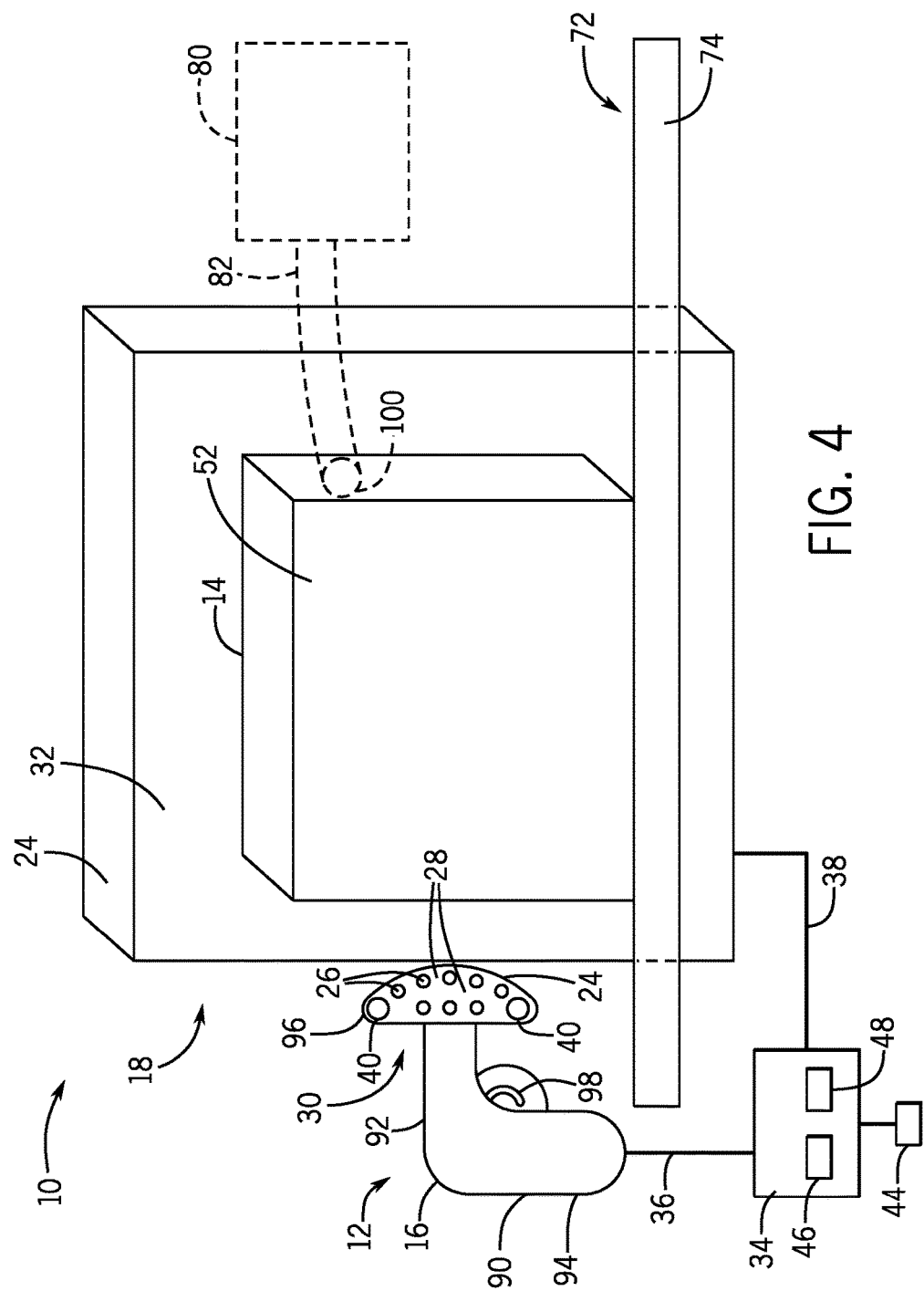
FIG. 4 is a schematic side view of an embodiment of a cold plasma treatment system, illustrating a handheld cold plasma applicator.

FIG. 4 is a schematic side view of an embodiment of a cold plasma treatment system 10 described in FIGS. 1 and 2 including a portable (e.g., handheld) applicator 90. For example, the cold plasma applicator 12 may include the first applicator portion 16 including the handheld applicator 90 coupled to the controller 34 via the first conductor 36. The handheld applicator 90 may include a body portion 92, a handle portion 94 configured to be held by an operator, a head or electrode portion 96, and a trigger 98 configured to control an ON/OFF state and/or intensity of the cold plasma generation (e.g., trigger 98 pulled to generate the cold plasma). The duration and/or frequency of the cold plasma generation may be controlled manually by an operator; however, in another embodiment, the cold plasma generation may be controlled by an operator as well as by the controller 34.

The head portion 96 may include a flat application surface or a curved application surface (e.g., arcuate surface, semi-spherical surface, etc.) as shown in FIG. 4. The head or electrode portion 96 may include one or more electrodes 26 secured by the applicator support 24 and coupled to the controller 34 via the first conductor 36. The head portion 96 also may include any configuration of one or more electrodes 26 as described herein, such as a single electrode or a spaced electrode pattern 30. There may be one or more sensors 40 disposed on the head or electrode portion 96 to monitor useful information, such as voltage, current, voltage waveforms, current waveforms, gas flow rate, gas concentration, positional data, plasma generation, plasma concentration, plasma intensity, plasma distribution, along with any other parameters disclosed herein to characterize the plasma generated. The one or more sensor 40 may be coupled to the controller 34 via wired or wireless connections. In operation, an operator may use the handheld applicator 90 to generate cold plasma within the container 14. For example, an operator may move the handheld applicator 90 back and forth over the exterior of the container 14 (e.g., may or may not directly contacting the container 14) to generate cold plasma in any part or portion of the container 14. The second applicator portion 18 (e.g., the ground electrode 32) may be disposed on the opposite side of the container 14 or adjacent to the container 14 relative to the handheld applicator 90. Accordingly, as the operator moves the handheld applicator 90 over the container 14, the cold plasma treatment system 10 generates cold plasma within the container 14. In certain embodiments, the second applicator portion 18 is a stationary unit, such as a stationary base. Accordingly, the container 14 may be disposed on the stationary base while the handheld applicator 90 is used to apply the cold plasma to the container 14.

In addition, the container 14 may include a gas inlet 100 capable of receiving gas (e.g., inert gas, helium, neon, argon, krypton, xenon, radon, oxygen, nitrogen, air, or any combination thereof) from the gas source 80 via the gas supply conduit 82, thus enabling production of specific or desired reactive species (e.g., species that kill bacteria) within the container 14. In some embodiments, the handheld applicator 90 may be used on the assembly line 72 alone or in combination with the automated packaging system 70 described in FIG. 3. For example, the handheld applicator 90 may be coupled to a robotic arm or other automated system, rather than being held by an operator. In some embodiments, the handheld applicator 90 may be used as a standalone unit (e.g., in a doctor's office, surgical room, etc.) not associated with the assembly line 72.

Figure 5:
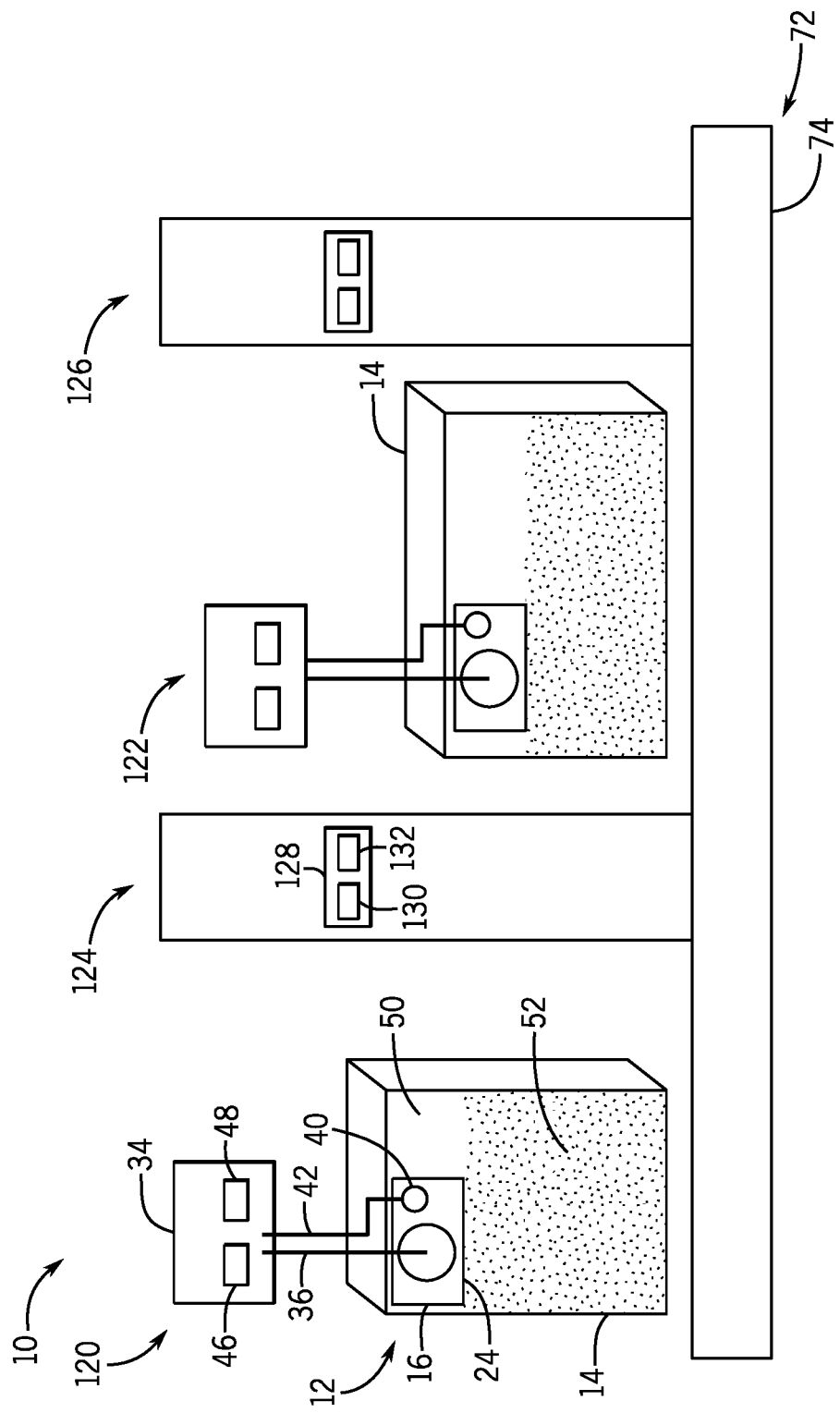
FIG. 5 is a schematic side view of an embodiment of a cold plasma treatment system with multiple stations of cold plasma treatment and robotics to reposition containers.

FIG. 5 is a schematic side view of the cold plasma treatment system 10 shown in FIG. 4 including one or more cold plasma treatment stations. For example, the cold plasma treatment system 10 may include a first cold plasma treatment station 120 and a second cold plasma treatment station 122, each configured in any manner disclosed herein, and each capable of generating cold plasma within a container or package 14. The automated conveyer 74 may be used to move the containers 14 along the assembly line 72 as described. In contrast to the cold plasma treatment system 10 descried above, the cold plasma treatment system 10 in FIG. 5 includes one or more robotics along the assembly line 72, each between two of the cold plasma treatment stations. For example, a first robotics station 124 may be stationed between the first and second cold plasma treatment stations 120 and 122, and a second robotics station 126 may be stationed after the second cold plasma treatment station 122 and before a third cold plasma treatment station or another automated station, and so on. The first and second robotics stations 124 and 126 may also be described as positioning stations, e.g., container reorientation stations.

Each of the robotics may include a controller 128 coupled to the power supply 44 or a separate power supply and include one or more processors 130 and one or more memories 132. The controller 128 may use the processor 130 to execute instructions stored in the memory 132 to perform operation on the containers 14 cooperatively with the cold plasma treatment received at each cold plasma treatment station. For example, the container 14 may receive cold plasma treatment pertained to a specific location/spot on the container 14 at first cold plasma station 120. Next, the container 14 moves along the assembly line 72 and arrives at the first robotics station 124, wherein the container 14 is rotated or otherwise repositioned (the contents 52 inside the container 14 may or may not be shifted during the operation). The container 14 then moves along the assembly line 72 and arrives at the second cold plasma treatment station 122 to receive cold plasma treatment associated with a different location/spot since the container has been rotated/repositioned. The container 14 may then continue to the second robotics station 126 that rotates or repositions the container 14 for additional cold plasma treatments or prepares the container 14 for transportation, shipping, etc. In this way, the cold plasma treatment system 10 may ensure improved or more complete sanitization and/or sterilization of the entire container.

FIG. 6 is a side view of an embodiment of a cold plasma applicator 12 used in the systems of FIGS. 1-5, illustrating a portable unit with handles 142, a controller 34, sensors 40, and a spaced electrode pattern 30 on a cold plasma application side 140. The cold plasma applicator 12 has the first applicator portion 16 with powered electrode 26, and may separately include the second applicator portion 18 with ground electrode 32 (see FIG. 1). As illustrated, the first applicator portion 16 includes the applicator support 24 having the cold plasma application side 140 with electrodes 26 and one or more handles 142 opposite to the cold plasma application side 140. The applicator support 24 may be made of electrically insulative material (e.g., an electrically insulative base) configured to secure the one or more electrode 26 on the cold plasma application side 140. For example, the applicator support 24 may be an electrically insulative plate or base with recesses, such that the one or more electrodes 26 are received by the corresponding recesses (e.g., interference fit, adhesion, molded in place, printed, etc.). The electrodes 26 may protrude a distance away from the cold plasma application side 140, thereby defining a non-flat surface. For example, the electrodes 26 may be configured in the spaced electrode pattern 30 (e.g., one or more continuous coils) with spaced electrode gaps 28 (e.g., uniform or variable gaps 28). For example, FIG. 7 shows a top view of the cold plasma applicator 12 on the cold plasma application side 140. As illustrated, the electrode 26 has a shape of a continuous coil (e.g., a spiraling or helical electrode) disposed on the cold plasma application side 140 (e.g., recessed, flush, or protruding) of the applicator support 24 and spirals from a central point and gets progressively farther away as it revolves around the center point with the electrode gap 28. The electrode gap 28 may be continuous or uniform with a substantially constant value. However, in some embodiments, the electrode gap may vary (e.g., progressively increase, progressively decrease, or alternatingly increase and decrease) as the electrode 26 spirals around the central point to define the coil. In some embodiments, the cold plasma application side 140 may include a plurality of spaced electrode patterns 30 offset from one another and/or interweaved with one another along the side 140.

The second applicator portion 18 may be disposed opposite to the cold plasma application side 140 in relation to a cold plasma treatment region 146. Furthermore, there may be one or more sensors 40 disposed along the applicator support 24 and coupled to the controller 34 for monitoring useful information related to the characteristics of the cold plasma generation. In operation, a user/operator may hold onto the one or more handles 142 and move the cold plasma applicator 12 around to cover various portions of the container 14 within the cold plasma treatment region 146. In some embodiments, the controller 34 may be configured to adjust the cold plasma applicator 12 in response to feedback from the one or more sensors 40. In some embodiments, the electrode 26 may include rounded edges to spread potential energy generated by the electrical signal and thus equalize cold plasma generation over the cold plasma treatment region 146. For example, the electrode 26 may have an arcuate or curved cross-section, such a concave surface geometry.

FIG. 8 is a side view of an embodiment of a cold plasma applicator 12 used in the systems of FIGS. 1-5, illustrating a portable unit with handles 142, a controller 34, sensors 40, and a spaced electrode pattern 30 with a pair of adjacent electrodes 26 (e.g., pair of adjacent electrode coils). In contrast to the cold plasma applicator 12 in FIGS. 6 and 7, the cold plasma applicator 12 in FIG. 8 includes an electrode pair 160 (see FIG. 8A) instead of a single electrode in the spaced electrode pattern (e.g., coil pattern). For example, the electrode pair 160 includes a first electrode 162 (e.g., coil) and a second electrode 164 (e.g., coil) overlapping with one another (e.g., parallel) with a gap 166 that offsets the first and second electrodes 162 and 164 in a planar direction (e.g., planar direction of a flat coil). The first and second electrodes 162 and 164 are coupled to the controller 34 via the first and second conductors 36 and 38, respectively (e.g., electrical conductor, wire, electrical cable, HV/RF cable, etc.). In operation, the first electrode 162 receives the multi-frequency, harmonic-rich electrical signal from the controller 34 and generates cold plasma, which is guided and/or drawn by the second electrode 164 of opposite charge. Accordingly, the cold plasma is generated between the first and second electrodes 162 and 164 (e.g., approximately around the gap 166) and also between each loop as the electrode pair 160 spirals from a central point and gets progressively farther away as it revolves around the center point with the electrode gap 28. It may be appreciated that since the second electrode 164 functions as the ground electrode 32 described above, the use of the electrode pair 160 in the cold plasma applicator 12 may eliminate the use of a separate ground electrode 32. It may also be appreciated that in some embodiments, the gap 166 and/or the electrode gap 28 may be adjusted separately or collectively to adjust the characteristics and coverage of the cold plasma generated.

Figure 9:
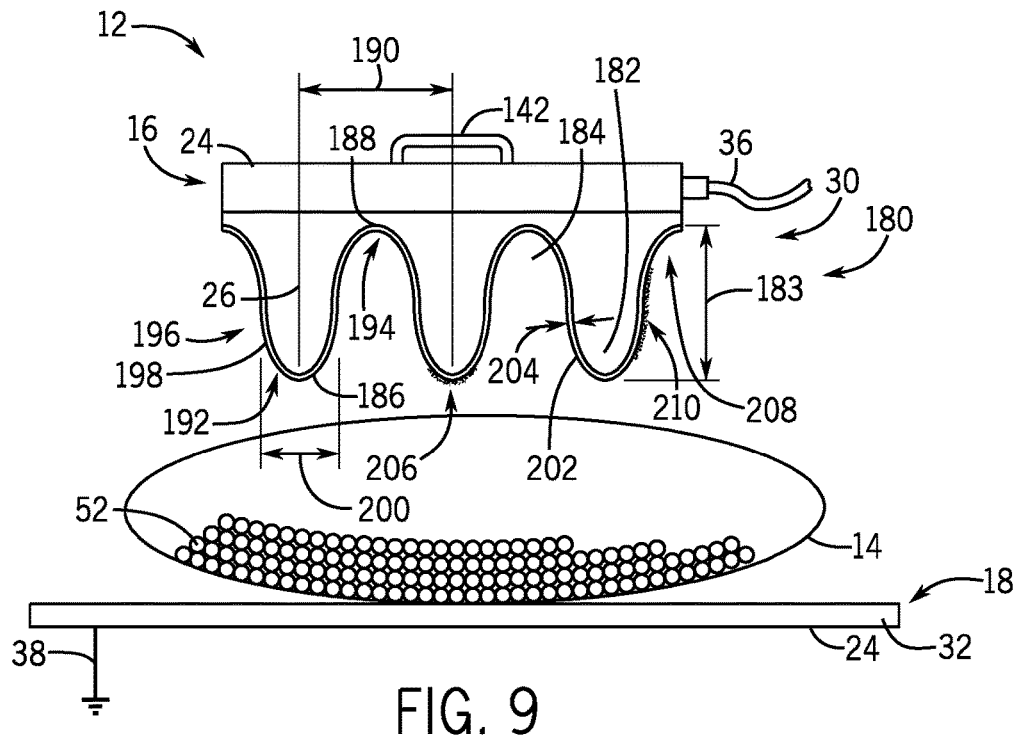
FIG. 9 is a side view of an embodiment of a cold plasma applicator used in the systems of FIGS. 1-5, illustrating a first applicator portion with a spaced electrode pattern (e.g., wavy plasma application surface) opposite from a second applicator portion having a planar surface.

FIG. 9 is a side view of an embodiment of a cold plasma applicator 12 used in the systems of FIGS. 1-5, illustrating a first applicator portion 16 with a spaced electrode pattern 30 (e.g., varying geometry application surface 180 with a wavy plasma application surface 196) opposite from a second applicator portion 18 having a planar surface. The cold plasma applicator 12 has the first applicator portion 16 with the powered electrode 26 along a varying geometry of the cold plasma application side 140 to define the spaced electrode pattern 30. As illustrated, the geometry of the electrode 26 varies inwardly and outwardly (e.g., curves inwardly and outwardly) to form the spaced electrode pattern 30. For example, the powered electrode 26 may include a varying geometry application surface 180 having a plurality of protruding electrode portions 182 spaced apart from one another to define a plurality of intermediate recessed portions 184. Each of the plurality of protruding electrode portions 182 has a height 183. As illustrated, each of the plurality of the protruding electrode portions 182 may include a tip (e.g., a highest point or peak) 186, and each of the plurality of intermediate recessed portions 184 may include a base 188 (e.g., a lowest point or nadir) such that each tip 186 is disposed between two bases 188, and each base 188 is disposed between two tips 186.

Furthermore, there may be a width 190 between adjacent tips 186 (or bases 188). Each tip 186 may have a curvature 192, and each base 188 may have a curvature 194 such that the electrode 26 has a wavy plasma application surface 196, which curves alternatingly in opposite directions (e.g., a wave pattern such as a sinusoidal wave pattern). Between the curvatures 192 and 194 there may be an alternating curvature 198 that transits the wavy plasma application surface 196 from curving in one direction to the next opposite direction, and there may be a distance 200 between adjacent alternating curvatures 198. A dielectric layer 202 (e.g., coating) of a thickness 204 is disposed over the electrode 26. In some embodiments, each of the width 190, the distance 200, the height 183, the curvatures 192 and 194, and the thickness 204 may be a constant throughout the entire wavy plasma application surface 196. In some embodiments, some or all of the width 190, the distance 200, the height 183, the curvatures 192 and 194, and the thickness 204 may vary at different portions of the wavy plasma application surface 196. Furthermore, the wavy plasma application surface 196 (e.g., the width 190, the distance 200, the height 183, and the curvatures 192 and 194) may be static or fixed in position, or the wavy plasma application surface 196 may be adjustable as discussed in further detail below with reference to FIGS. 14 and 15. The thickness 204 of the dielectric layer 202 may be a constant value (e.g., uniform thickness) or it may vary along the varying geometry application surface 180 (e.g., variable thickness). For example, the thickness 204 may be greater along the plurality of the protruding electrode 182 and lesser along the plurality of the intermediate recessed portions 184. The variable thickness 204 may help to increase the plasma generation along the wavy plasma application surface 196.

There may be cold plasma generation regions throughout the entire varying geometry application surface 180 including a first plasma generation region 206 around the plurality of protruding electrode portions 182, a second plasma generation region 208 around the plurality of the intermediate recessed portions 184, and a third plasma generation region 210 around the alternating curvatures 198. Within a fixed dimension (e.g., dimension of the applicator support 24), the total area of the plasma generation region is larger for the varying geometry application surface 180 (e.g., wavy plasma application surface 196) as compared to a substantially flat application surface (e.g., a flat electrode plate). As such, it may be appreciated that the cold plasma applicator 12 with the varying geometry applications surface 180 may treat contents 52 more efficiently due to the enlarged surface area of the cold plasma generation region. It may also be appreciated that in operation, an operator may press the cold plasma applicator 12 onto the container 14 (e.g., via the handle 142), such that the container 14 (e.g., a package, a bag, a soft container, etc.) may deform to comply with the varying geometry application surface 180, which reduces distances between the electrode 26 and the contents 52 to be treated, and thereby improves the treatment efficiency of the cold plasma applicator 12. The varying geometry application surface 180 also creates spaces (e.g., intermediate recessed portions 184 between the protruding electrode portions 182) that may help to increase generation of the cold plasma, thereby improving the efficiency of the cold plasma applicator 12.

As mentioned earlier, the curvatures 192 and 194 that outline the tip 186 and base 188 of the protruding electrode portion 182 and the intermediate recessed portion 184 may vary and result in different varying geometry applications surfaces 180. In other words, the curvatures 192 and 194 may have various radii of curvature, which also vary the width 190, the distance 200, the height 183, and other characteristics of the surfaces 180. In some embodiments, the curvatures 192 and 194 may be combined and/or replaced with other surface geometries, such as flat surfaces, angled surfaces, textured surfaces, or any combination thereof.

Figure 10:
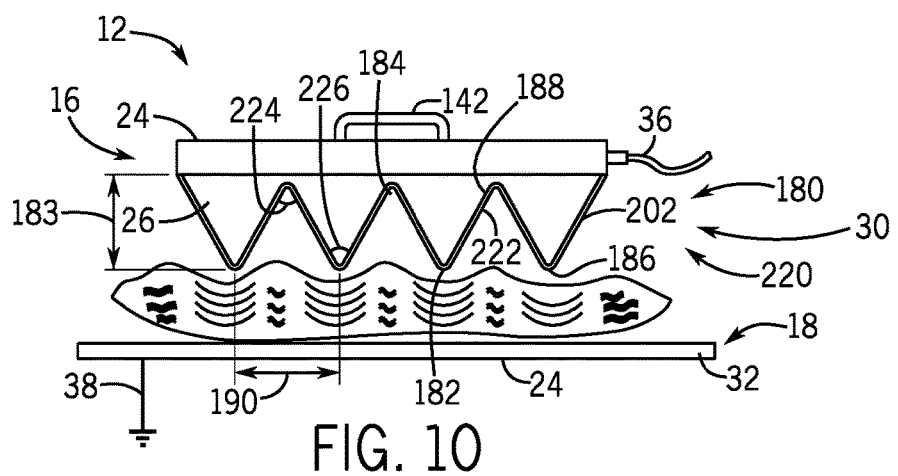
FIG. 10 is a side view of an embodiment of a cold plasma applicator used in the systems of FIGS. 1-5, illustrating a first applicator portion with a spaced electrode pattern (e.g., zigzagging plasma application surface) opposite from a second applicator portion having a planar surface.

FIG. 10 is a side view of an embodiment of a cold plasma applicator 12 used in the systems of FIGS. 1-5, illustrating a first applicator portion 16 with a spaced electrode pattern 30 (e.g., zigzagging plasma application surface 220) opposite from a second applicator portion 18 having a planar surface. The zigzagging plasma application surface 220 has the plurality of protruding electrode portions 182 and the plurality of intermediate recessed portions 184, wherein the zigzagging plasma application surface 220 turns alternatingly in opposite directions with flat angled surfaces 222 as shown in FIG. 10. As described above, each of the plurality of the protruding electrode portions 182 may include a tip (e.g., peak) 186 and each of the plurality of intermediate recessed portions 184 may include a base 188 (e.g., nadir). In the embodiment of FIG. 10 compared with the embodiment of FIG. 9, each tip 186 may have a more sharp turn or smaller radius of curvature, each base 188 may have a more sharp turn or smaller radius of curvature relative to the embodiment of FIG. 9. In particular, and alternating flat angled surfaces 222 extend between the adjacent tips 186 and bases 188. For example, the zigzagging plasma application surface 220 has an angle 224 between adjacent alternating flat angled sides 222 around the intermediate recessed portion 184 and an angle 226 between adjacent alternating flat angled sides 222 around the protruding electrode portion 182. In some embodiments, the angles 224 and 226 may be of a same value, and in other embodiments, the angles 224 and 226 may be different (e.g., gradually increasing, decreasing, or alternating). In some embodiments, each of angles 224 and 226 may be a constant value throughout the entire zigzagging plasma application surface 220. In some embodiments, some or all of the angles 224 and 226 may vary at different portions of the zigzagging plasma application surface 220.

Figure 11:
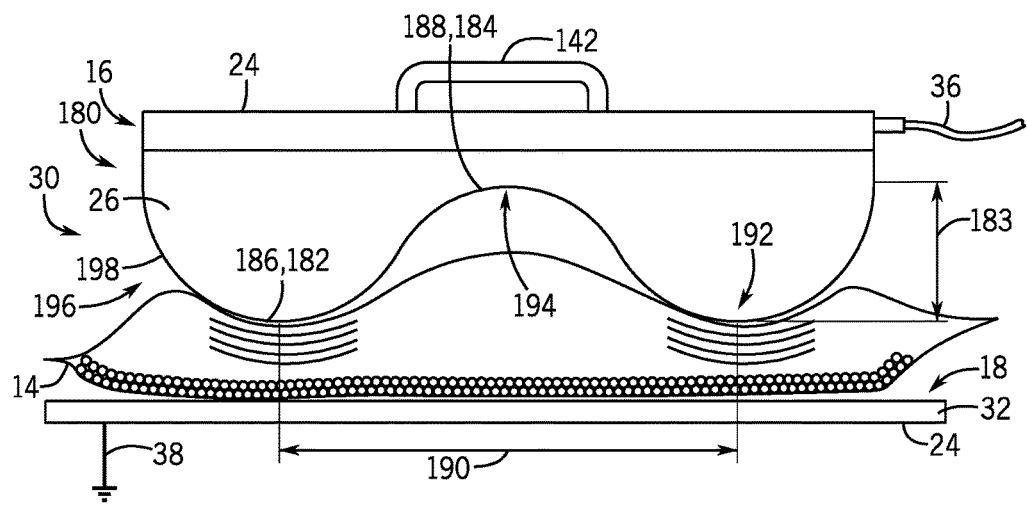
FIG. 11 is a side view of an embodiment of a cold plasma applicator used in the systems of FIGS. 1-5, illustrating a first applicator portion with a spaced electrode pattern (e.g., recess between a pair of protrusions) and a second applicator portion with a planar surface.
Figure 12:
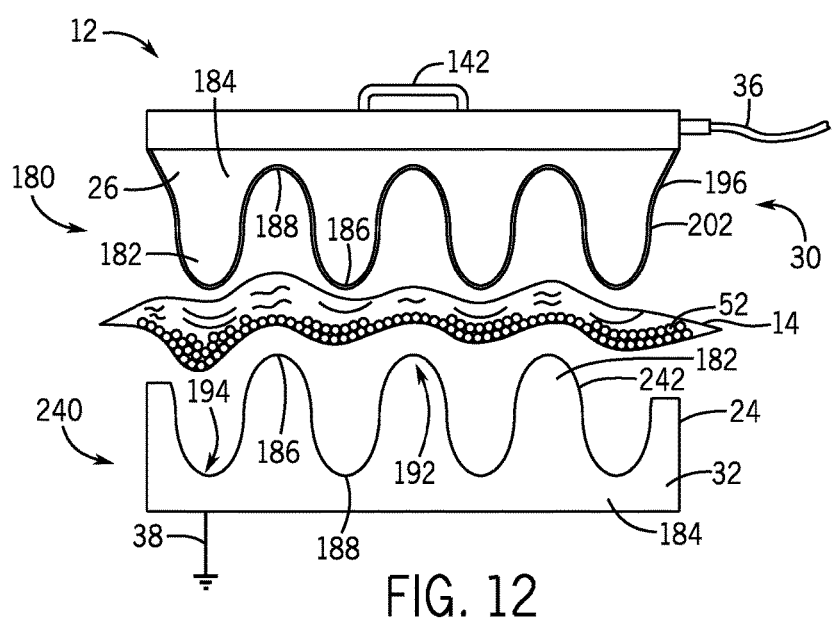
FIG. 12 is a side view of an embodiment of a cold plasma applicator used in the systems of FIGS. 1-5, illustrating first and second applicator portions opposite from one another and including spaced electrode patterns (e.g., wavy surfaces)

FIG. 11 is a side view of an embodiment of a cold plasma applicator 12 used in the systems of FIGS. 1-5, illustrating a first applicator portion 16 with a spaced electrode pattern 30 (e.g., recess 184 between a pair of protrusions 182) and a second applicator portion 18 with a planar surface. Note that as mentioned above, there may not be the dielectric coating 202 on the one or more electrodes 26. For example, the container 14 may be made of a dielectric material and act as a dielectric barrier such that the dielectric coating 202 may not be required. Similar to the embodiment of FIG. 9, the cold plasma applicator 12 has the wavy plasma application surface 196 with the plurality of protruding electrode portions 182 and the one intermediate recessed portion 184, while the curvatures 192 and 194 are more gradual (e.g., greater radii of curvature), the height 183 is reduced, and the width 190 is increased as compared to that illustrated in FIG. 9. In certain applications, the wavy plasma application surface 196 of FIG. 11 may be more suitable and effective at providing cold plasma treatment for a particular container 14 and its contents. As described above, the varying geometry application surfaces 180 in FIGS. 9-11 may contribute to more efficient cold plasma treatment for at least the reasons discussed above (e.g., larger cold plasma generation area and appropriate distance between the electrode and the contents to be treated). Relating to this effect, in additional to the varying geometry application surface 180, the ground electrode 32 secured by the applicator support 24 of the second applicator portion 18 may correspondingly have a varying geometry ground surface 240 as illustrated in FIG. 12. The varying geometry ground surface 240 may be shaped and positioned similarly or differently relative to the varying geometry application surface 180. For example, in the illustrated embodiment, the varying geometry ground surface 240 may be similarly shaped and aligned with the varying geometry application surface 180, such that the surfaces 180 and 240 fit together (e.g., partially protrude into one another). The ground electrode 32 may include the structural features (e.g., the plurality of protruding electrode portions 182, the plurality of intermediate recessed portion 184, the tips 186, the bases 188, and the curvatures 192 and 194) discussed above with reference to the electrode 26. In certain embodiments, the varying geometry ground surface 240 may form a wavy ground surface 242. The wavy surfaces 196 and 242 may be aligned with one another, such that the opposite protruding electrode portions 182 align with one another and the opposite intermediate recessed portion 184 align with one another. In the illustrated embodiment, the wavy surfaces 196 and 242 are staggered relative to one another, such that the protruding electrode portions 182 align with the opposite intermediate recessed portions 184.

It may be appreciated that the cold plasma applicator 12 with the varying geometry application surface 180 (e.g., the wavy plasma application surface 196 and/or the zigzagging plasma application surface 220) may be suitable for treating the container 14 (e.g., soft container, bag, package, etc.) and the contents 52 under different conditions (e.g., deformability, conformability, the content to gas ratio, etc.). For example, if the shape of the container 14 cannot be easily deformed (e.g., bulky, less compliant, etc.) and/or the distribution of the contents 52 inside the container 14 cannot be easily re-distributed, one of the illustrated applicators 12 may provide more efficient production and distribution of cold plasma to treat the container 14 and its contents.

Figure 13:
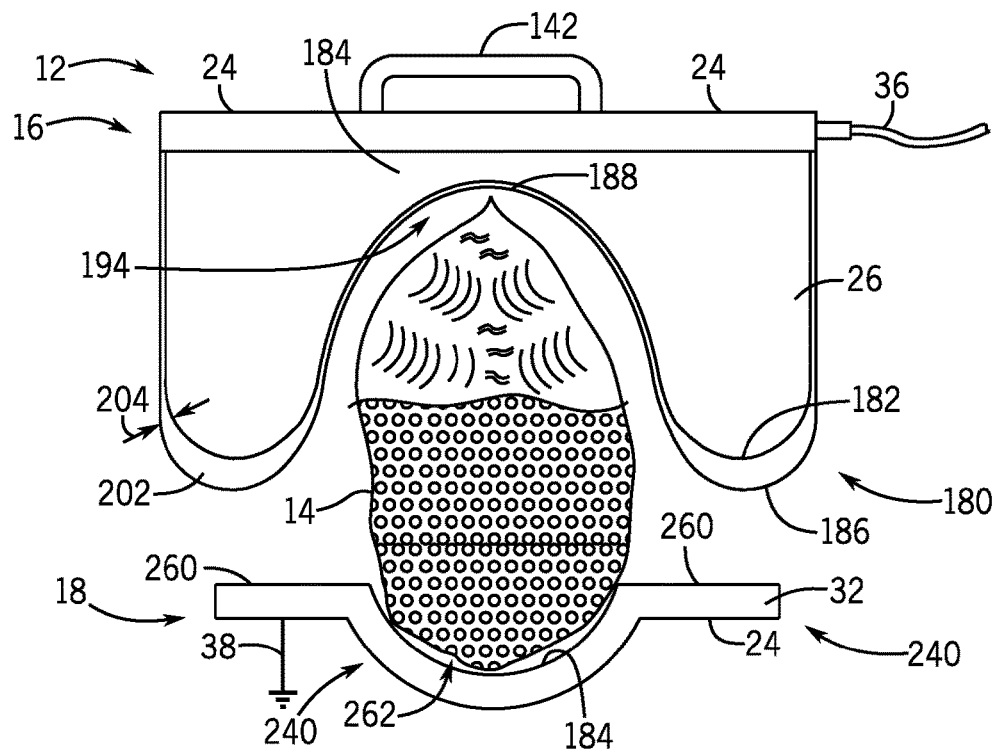
FIG. 13 is a side view of an embodiment of a cold plasma applicator used in the systems of FIGS. 1-5, illustrating a first applicator portion with a spaced electrode pattern (e.g., recess between a pair of protrusions) and a second applicator portion with a spaced electrode pattern (e.g., a recess between opposite portions of a planar surface)

Still in another embodiment, the cold plasma applicator 12 may include the first applicator portion 16 and the second applicator portion 18 configured collectively to encompass the container 14. In contrast to the cold plasma applicator 12 in FIG. 12, the cold plasma applicator 12 in FIG. 13 includes the varying geometry application surface 180 and the varying geometry ground surface 240 shaped/configured accordingly to substantially encompass the container 14. For example, the first applicator portion 16 may include the powered electrode 26 secured by the applicator support 24, which may be substantially flat. The electrode 16 may include the plurality of protruding electrode portions 182, each locates close to an edge of the applicator support 24, and the intermediate recessed portion 184 close to a center of the applicator support 24. As illustrated, each of the plurality of the protruding electrode portions 182 may include a tip (e.g., peak) 186, and the plurality of intermediate recessed portions 184 may include a base 188 (e.g., nadir) such that the base 188 is between the two tips 186.

Accordingly, the cold plasma applicator 12 may include the ground electrode 32 secured by the applicator support 24 of the second applicator portion 18, wherein the ground electrode 32 may include a flat portion 260 and an intermediate recessed portion 184. The intermediate recessed portion 184 of the second applicator portion 18 is directly opposite to the intermediate recessed portion 184 of the first applicator portion 16, such that the container 14 may be encompassed or at least substantially enclosed by the first and second applicator portions 16 and 18. As described above, the base 188 has the curvature 194, and likewise, the intermediate recessed portion 184 of the second applicator portion 18 may also have a curvature 262. Both of the curvatures 194 and 262 may vary individually or collectively to adjust the shape/volume of the enclosed volume between the first and second applicator portions 16 and 18. Furthermore, the dielectric layer 202 (e.g., coating) of the thickness 204 is disposed over the electrode 26 (e.g., conductive material). In some embodiments, the thickness 204 of the dielectric layer 202 may be a constant value or it may vary along the varying geometry application surface 180. For example, the thickness 204 may be greater along the plurality of the protruding electrode portions 182 (e.g., tips 186) and lesser along the intermediate recessed portion 184 (e.g., base 188). In this manner, the varying thickness 204 may help to control and increase the generation of cold plasma for treating the container 14 and its contents.

Figure 14:
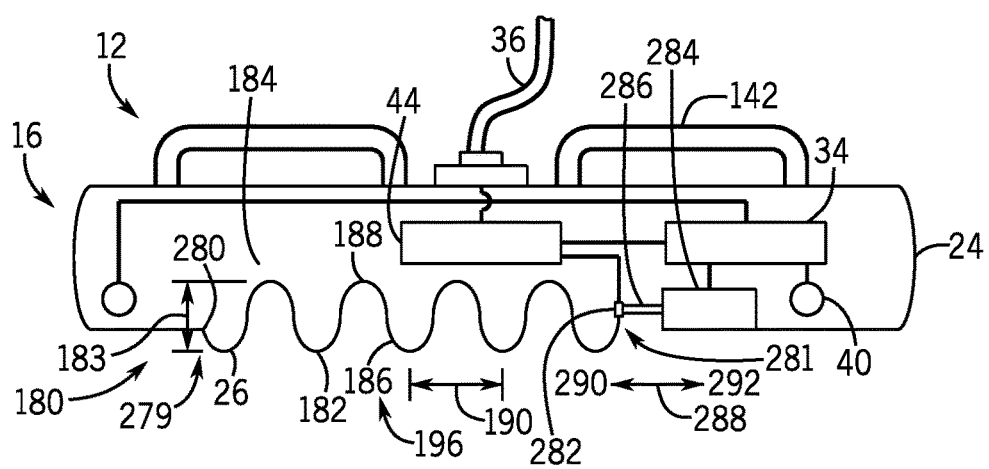
FIG. 14 is a side view of an embodiment of a cold plasma applicator used in the systems of FIGS. 1-5, illustrating a spaced electrode pattern that is adjustable via a drive and controller, wherein the spaced electrode pattern is disposed in a first configuration (e.g., expanded configuration)

Furthermore, in some embodiments, the varying geometry application surface 180 may be adjustable as discussed below in FIGS. 14 and 15. FIG. 14 is a side view of the first applicator portion 16 of the cold plasma applicator 12, including the electrode 26 having the varying geometry application surface 180, which is adjustable. The electrode 26 may have the wavy plasma application surface 196 including the plurality of protruding electrode portions 182 and the plurality of intermediate recessed portions 184, and the wavy plasma application surface 196 curves alternatingly in opposite directions. As illustrated, each of the plurality of the protruding electrode portions 182 may include the tip (e.g., peak) 186, and each of the plurality of intermediate recessed portions 184 may include the base 188 (e.g., nadir) such that each tip 186 is adjacent to two bases 188, and each base 188 is adjacent to two tips 186. Furthermore, the width 190 is defined as the distance between adjacent tips 186, and the height 183 is defined as the peak-to-peak amplitude (e.g., the distance from the base 188 to the tip 186).

The electrode 26 may be secured in the applicator support 24 such that any changes in the shape/dimension of the varying geometry application surface 180 may be accommodated. For example, the electrode 26 may be disposed within an empty space of the applicator support 24. A first ending portion 279 of the electrode 26 may be secured to the applicator support 24 via a first joint 280 while a second ending portion 281 of the electrode 26 may be coupled to a shaft 286 via a second joint 282. The shaft 286 may couple to a drive 284, which is coupled to the controller 34. Upon receiving electrical signals from the controller 34, the drive 284 may drive the shaft 286 to move the second joint 282 in an axial movement 288 (e.g., in directions parallel to a longitudinal direction of the electrode 26, directions tangent to the first and second joints 280 and 282). As the second joint 282 is driven to move back and forth in the axial movement 288, the shape/dimension (e.g., the width 190, the height 183, the curvature 192 and 194, or a combination thereof) of the varying geometry application surface 180 changes accordingly since the first joint 280 is secured without the freedom of the axial movement 288.

Figure 15:
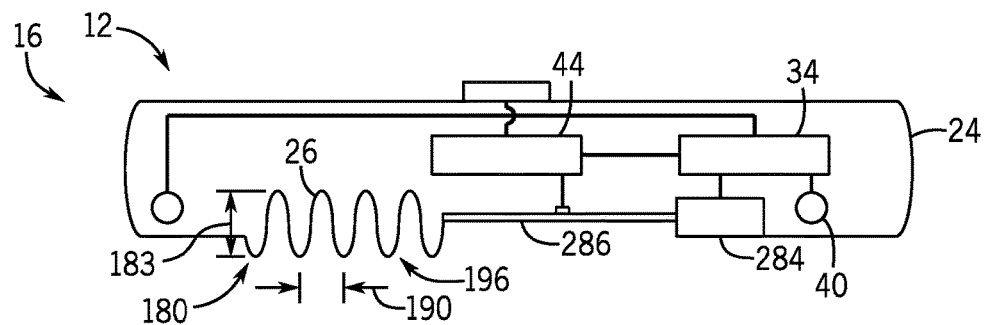
FIG. 15 is a side view of an embodiment of the cold plasma applicator of FIG. 14 used in the systems of FIGS. 1-5, illustrating the spaced electrode pattern in a second configuration (e.g., contracted configuration)

For example, when the axial movement 288 is in a first direction 290 (e.g., the electrode 26 under compression), the width 190 of the plurality of the intermediate recessed portion 184 (or the plurality of the protruding electrode portion 182) may decrease while the height 183 of the plurality of the intermediate recessed portion 184 (or the plurality of the protruding electrode portion 182) increase, as shown in FIG. 15. Contrarily, when the axial movement 288 is in a second direction 292 (e.g., the electrode 26 under tension), the width 190 of the plurality of the intermediate recessed portion 184 (or the plurality of the protruding electrode portion 182) may increase while the height 183 of the plurality of the intermediate recessed portion 184 (or the plurality of the protruding electrode portion 182) decrease. In some embodiments, the controller 34 coupled to the drive 284 may adjust the width 190 and the height 183 of the varying geometry application surface 180 in response to the sensor feedback from the one or more sensors 40. In this manner, the controller 34 may adjust the geometry of the varying geometry application surface 180 to increase plasma generation for a particular application, e.g., container geometry, container rigidity or flexibility, container contents, or any combination thereof.

Figure 16:
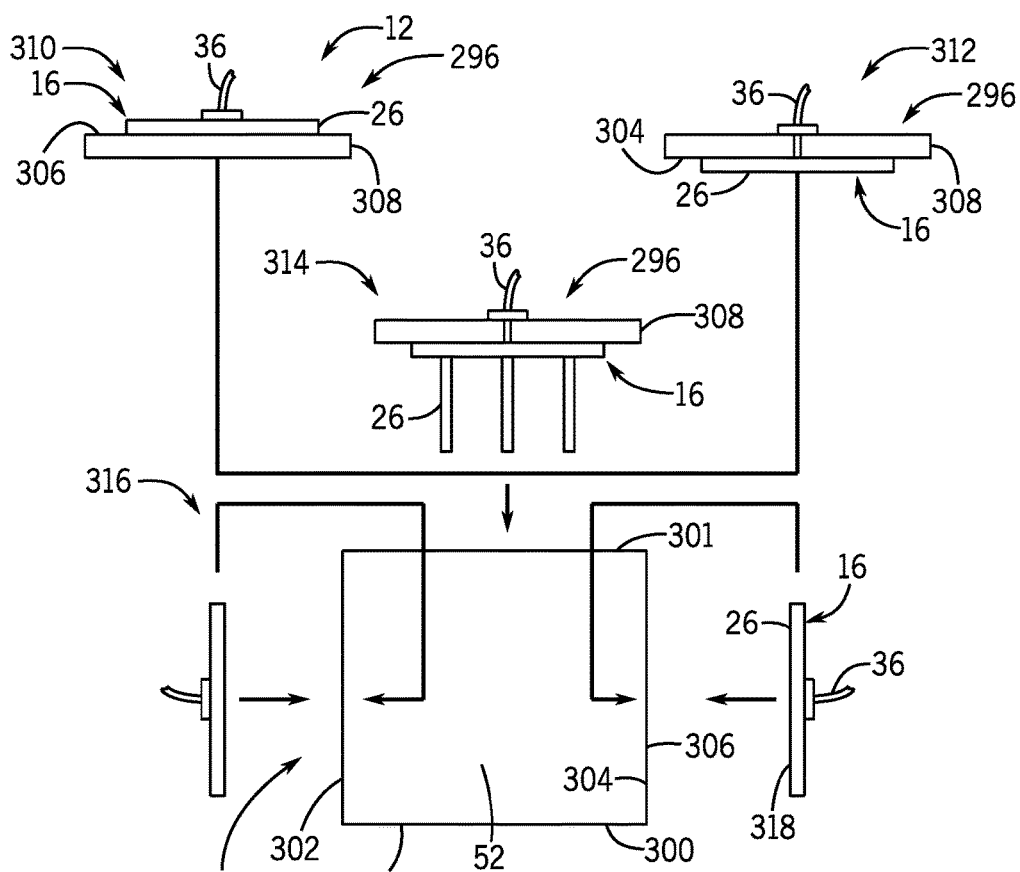
FIG. 16 is an exploded side view of an embodiment of a cold plasma treatment system having one or more cold plasma applicators configured to mount on various portions of a container, such as inside and outside of a cover portion and a container portion.

In certain embodiments, the cold plasma applicator 12 may couple to an interior and/or an exterior of the container 14 as discussed below. FIG. 16 is an exploded side view of an embodiment of a cold plasma treatment system 10 having one or more cold plasma applicators 12 configured to mount on various portions of a container 14, such as inside and outside of a cover portion 296 and a container portion 298. As illustrated, the container portion 298 of the container 14 may include a base 300, an open top 301, and one or more side walls 302, while the cover portion 296 has a cover or lid structure 308 configured to close the container portion 298 as to enclose/seal the contents 52 inside the container 14. The cover portion 296 and the container portion 298 also may have an interior 304 and an exterior 306. As discussed above, the cold plasma applicator 12 includes the first applicator portion 16 with the powered electrode 26 and the second applicator portion 18, which may be opposite to and adjacent to the first applicator portion 16 (e.g., for guiding the generated cold plasma). In certain embodiments, the first and second applicator portions 16 and 18 may be integrated together in a single applicator 12 (e.g., the first applicator portion 16).

As illustrated, the first applicator portion 16 may be coupled to and/or integrated with the cover portion 296 and/or the container portion 298 by any suitable coupling, such as an adhesive, a thermal bond, a chemical bond, a printed layer (e.g., printing directly onto the surface), a fastener (e.g., threaded fastener, a snap-fit coupling, a latch, a clamp, etc.), molding in place within the cover 308, or any combination thereof. For example, the first applicator 16 may couple to the cover portion 296 on the side of the exterior 306 as shown in a configuration 310, or on the side of the interior 304 as shown in a configuration 312. By further example, the first applicator 16 may couple to the container portion 298 on the side of the exterior 306 and/or on the side of the interior 304. On the container portion 298, the first applicator portion 16 may be attached to the side wall 302 (e.g., any sides of the side wall 302), the base 300, or any combination thereof.

The first applicator portion 16 also may have a variety of configurations, such as any of the configurations disclosed herein. For example, the electrode 26 may take form of any aforementioned shape or dimension, including sheet, plate, coil, wavy surface, zigzagging surface, etc. In some embodiments, the electrode 26 of the first applicator 16 may be coupled to the container 14, such that the longitudinal direction or planar direction of the electrode 26 is parallel to the cover portion 296 (e.g., lie relatively flat on the cover 308) and/or parallel to the container portion 298. In some embodiments, the electrode 26 of the first applicator 16 may be coupled to the container 14, such that the electrode 26 protrudes, hangs, or is arranged in a cantilevered manner relative to the surface of the container portion 298 and/or the surface of the cover portion 296 as shown in a configuration 314. In operation, the container 14 may be sealed/closed with the cover 308 closing the open top 301, and the cold plasma is generated to treat (e.g., clean, sterilize, sanitize, etc.) the contents 52 enclosed inside the container 14.

Again, in certain embodiments, the second applicator portion 18 may be integrated with the first applicator portion 16, or both applicator portions 16 and 18 may be coupled to different portions of the container 14 (e.g., interior 304 or exterior 306 of the cover and container portions 296 and 298), or the applicator portion 18 may be used separate from the container 14.

Figure 17:
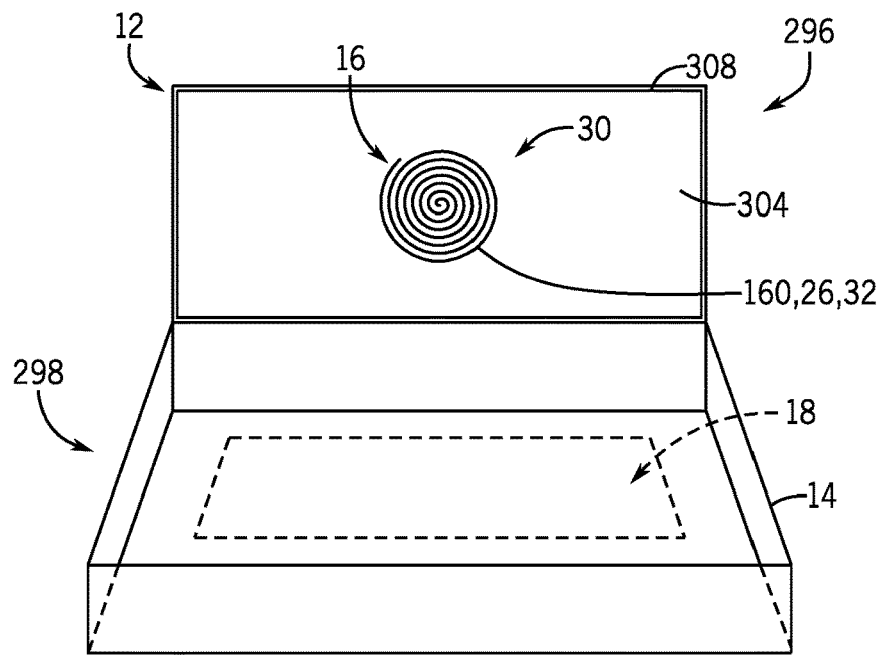
FIG. 17 is a side view of an embodiment of a cold plasma treatment system, illustrating a cold plasma applicator coupled to a cover of a container.

FIG. 17 is a side view of an embodiment of a cold plasma treatment system 10, illustrating a cold plasma applicator 12 coupled to a cover 308 of a container 14. As illustrated, the first applicator portion 16 couples to the cover 308 of the container 14 on the interior 304 side. In certain embodiments, both of the powered and ground electrodes 26 and 32 (e.g., the electrode pair 160) are included in the first applicator portion 16. In some embodiments, the first applicator portion 16 is coupled to the cover 308, while the second applicator portion 18 may be coupled to or integrated with the container portion 298. In either configuration, the cold plasma applicator 12 may be configured to generate the cold plasma when the cover 308 is closed relative to the container portion 298.

Figure 18:
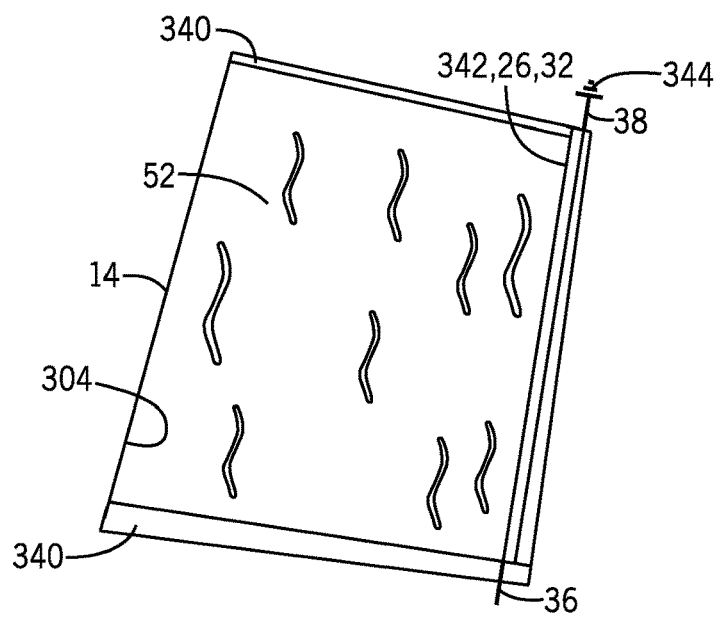
FIG. 18 is a side view of an embodiment of a cold plasma treatment system, illustrating a cold plasma applicator coupled to a wall of a container.

In addition, the embodiments described herein are not limited to having the powered electrode 26 and ground electrode 32 secured in the applicator support 24. Instead, the powered electrode 26 and ground electrode 32 may be integrated (e.g., embedded, adhered, printed, etc.) with the container or package 14. FIG. 18 shows a schematic side view of the container or package 14 with both the powered electrode 26 and the ground electrode 32 sealed inside the container 14. The container or package 14 may include one or more sealed portions 340 and an electrode assembly 342 including both the powered electrode 26 and the ground electrode 32. The electrode assembly 342 may be embedded into, printed onto, or adhered on the interior 304 of the container or package 14. The electrode assembly 342 also may include the first conductor 36 connecting the powered electrode 26 to the controller 34, and the second conductor 38 connecting the ground electrode 32 to a ground 344. For example, each of the first and second conductors 36 and 38 may include a first, a second, and a third portion. The first portion of each of the conductors 36 and 38 may be inside the container or package 14, the second portion may be sealed within the sealed portion 340, while the third portion may be exposed outside of the container or package 14 as to allow access to receive an electrical connection. In operation, the powered electrode 26 receives the multi-frequency, harmonic-rich electrical signal from the controller 34 and generates cold plasma inside the container or package 14.

It may be appreciated that a such container or package 14 described above (e.g., with the built-in electrode assembly 342) may offer significant freedom and flexibility in terms of applying cold plasma treatments at any time and any location as along as the power supply 44 and/or the HV/RF feed cable 144 are available. For example, the contents 52 may be sealed inside the above mentioned container or package 14 at the time of packaging. The cold plasma treatment may be performed at the time of packaging and/or the cold plasma treatment may also be performed at a later time and/or at locations other than the original packaged location (e.g., after the shipment of the container or package 14) as needed.

Figure 19:
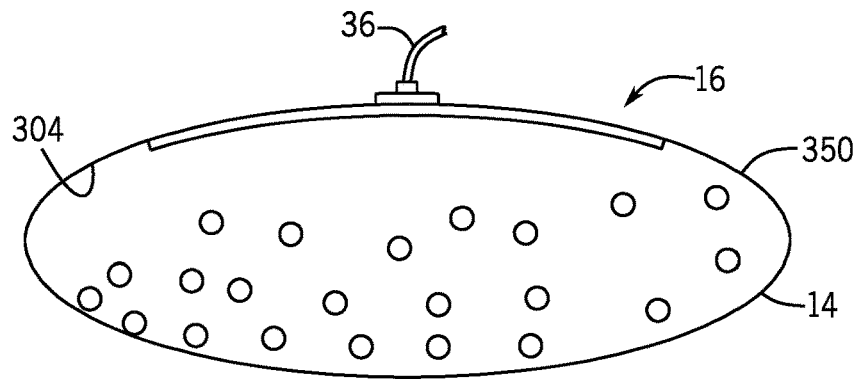
FIG. 19 is a side view of an embodiment of a cold plasma treatment system, illustrating a cold plasma applicator coupled to the interior of a wall of a container.
Figure 20:
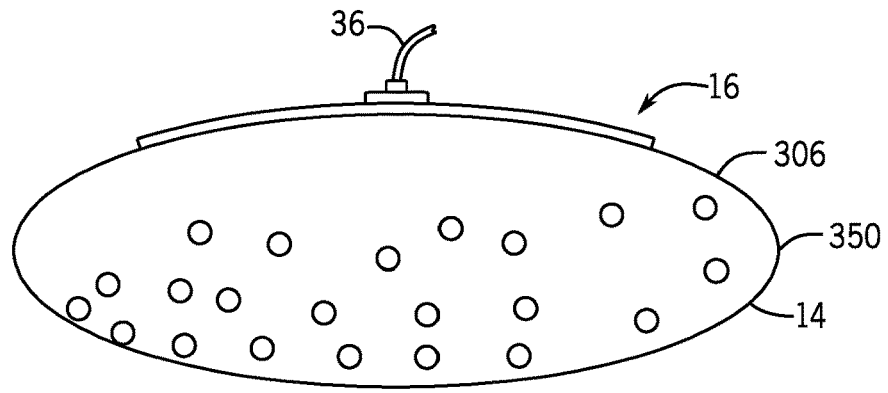
FIG. 20 is a side view of an embodiment of a cold plasma treatment system, illustrating a cold plasma applicator coupled to the exterior of a wall of a container.
Figure 21:
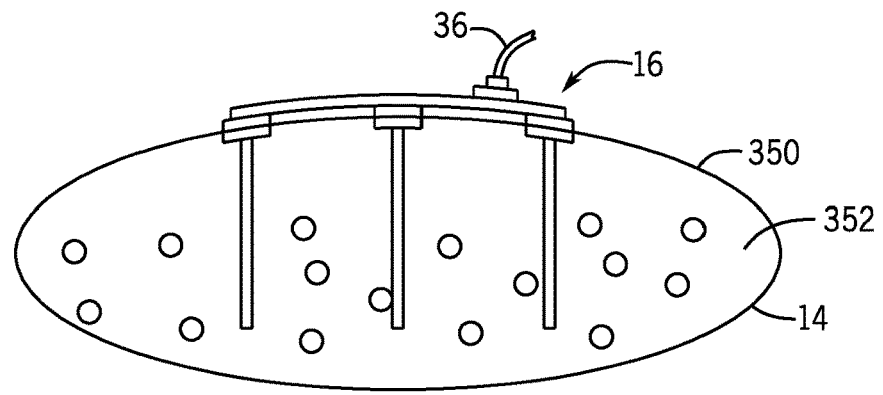
FIG. 21 is a side view of an embodiment of a cold plasma treatment system, illustrating a cold plasma applicator coupled to the wall of a container and protruding or hanging in an interior chamber of the container.

In certain embodiments, the container 14 may be a flexible container or package, such as a flexible bag as illustrated in FIGS. 19, 20, and 21. FIG. 19 is a side view of an embodiment of a cold plasma treatment system 10, illustrating a cold plasma applicator 12 (e.g., first applicator portion 16) coupled to the interior 304 of a wall 350 of a container 14 (e.g., sealed flexible bag). FIG. 20 is a side view of an embodiment of a cold plasma treatment system 10, illustrating a cold plasma applicator 12 (e.g., first applicator portion 16) coupled to the exterior 306 of a wall 350 of a container 14 (e.g., sealed flexible bag). FIG. 21 is a side view of an embodiment of a cold plasma treatment system 10, illustrating a cold plasma applicator 12 (e.g., first applicator portion 16) coupled to the wall 350 of a container 14 and protruding or hanging in an interior chamber 352 of the container 14.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A system, comprising:
a cold plasma applicator configured to generate a cold plasma within a container, wherein the cold plasma applicator comprises a varying geometry application surface having a plurality of protruding electrode portions spaced apart from one another to define a plurality of intermediate recessed portions, and wherein the varying geometry application surface is adjustable; and
a controller coupled to a drive and one or more sensors, wherein the controller is configured to control the drive to adjust a width or a depth of said application surface in response to sensor feedback from the one or more sensors.

2. The system of claim 1, wherein the cold plasma applicator has a wavy plasma application surface having the plurality of protruding electrode portions and the plurality of intermediate recessed portions, wherein the wavy plasma application surface curves alternatingly in opposite directions.

3. The system of claim 1, wherein the cold plasma applicator has a zigzagging plasma application surface having the plurality of protruding electrode portions and the plurality of intermediate recessed portions, wherein the zigzagging plasma application surface turns alternatingly in opposite directions.

4. The system of claim 1, comprising a conductive material defining the plurality of protruding electrode portions, and a dielectric layer disposed over the conductive material, wherein the dielectric layer is configured to interface with an outer surface of the container.

5. The system of claim 4, wherein a thickness of the dielectric layer varies along the varying geometry application surface.

6. The system of claim 5, wherein the thickness of the dielectric layer is greater along the plurality of protruding electrode portions and lesser along the plurality of intermediate recessed portions.

7. The system of claim 1, comprising a ground structure configured to be disposed on an opposite side of the container relative to the cold plasma applicator.

8. The system of claim 7, wherein the ground structure comprises a planar ground surface.

9. The system of claim 7, wherein the ground structure comprises a varying geometry ground surface having a plurality of protruding ground portions spaced apart from one another to define a plurality of intermediate recessed ground portions.

10. A system, comprising:
a cold plasma applicator configured to generate a cold plasma within a container, wherein the cold plasma applicator comprises a varying geometry application surface having a plurality of protruding electrode portions spaced apart from one another to define a plurality of intermediate recessed portions, and wherein the cold plasma applicator comprises a drive coupled to the varying geometry application surface to adjust a width of the plurality of the intermediate recessed portions, a depth of the plurality of intermediate recessed portions, or a combination thereof.

11. The system of claim 10, wherein the cold plasma applicator has a wavy plasma application surface having the plurality of protruding electrode portions and the plurality of intermediate recessed portions, wherein the wavy plasma application surface curves alternatingly in opposite directions.

12. The system of claim 10, wherein the cold plasma applicator has a zigzagging plasma application surface having the plurality of protruding electrode portions and the plurality of intermediate recessed portions, wherein the zigzagging plasma application surface turns alternatingly in opposite directions.

13. The system of claim 10, comprising a controller coupled to the drive and one or more sensors, wherein the controller is configured to control the drive to adjust the width or the depth in response to sensor feedback from the one or more sensors.

14. The system of claim 10, comprising a conductive material defining the plurality of protruding electrode portions, and a dielectric layer disposed over the conductive material, wherein the dielectric layer is configured to interface with an outer surface of the container.

15. The system of claim 14, wherein a thickness of the dielectric layer varies along the varying geometry application surface.

16. The system of claim 15, wherein the thickness of the dielectric layer is greater along the plurality of protruding electrode portions and lesser along the plurality of intermediate recessed portions.

17. The system of claim 10, comprising a ground structure configured to be disposed on an opposite side of the container relative to the cold plasma applicator.

18. The system of claim 17, wherein the ground structure comprises a planar ground surface.

19. The system of claim 17, wherein the ground structure comprises a varying geometry ground surface having a plurality of protruding ground portions spaced apart from one another to define a plurality of intermediate recessed ground portions.

20. The system of claim 10, comprising the container having food contents or medical contents.

* * * * *